United States Patent [19]

Zarchy et al.

[11] Patent Number: 4,709,116
[45] Date of Patent: Nov. 24, 1987

[54] ISOMERIZATION PROCESS AND APPARATUS

[75] Inventors: Andrew S. Zarchy, Amawalk; Warren K. Volles, Mt. Kisco; Luke F. O'Keefe, White Plains, all of N.Y.

[73] Assignee: Union Carbide Corporation, Danbury, Conn.

[21] Appl. No.: 879,909

[22] Filed: Jun. 30, 1986

[51] Int. Cl.$^4$ .............................................. C07C 5/13
[52] U.S. Cl. ................................... 585/738; 422/129; 422/234
[58] Field of Search ............... 585/738; 422/129, 234·

[56] References Cited

FOREIGN PATENT DOCUMENTS 626829 9/1961 Canada ................................ 585/738

Primary Examiner—Curtis R. Davis
Attorney, Agent, or Firm—Eugene Lieberstein

[57] ABSTRACT

The octane of a hydrocarbon feed is upgraded to make it suitable for use as a base stock for blending gasoline. An adsorber-lead system first removes non-normals from the feed and then subjects the normals to an isomerization reaction. The non-normals are then combined with at least a portion, preferably at least 50%, of the isomerization hydrocarbon product to form a product with a research octane number at least two units, preferably at least six units, greater than that of the feed.

20 Claims, 2 Drawing Figures 4,709,116

ISOMERIZATION PROCESS AND APPARATUS

TECHNICAL FIELD

This invention relates to improvements in processing and apparatus for upgrading the octane of a mixed hydrocarbon feedstock by partially isomerizing normal paraffinic hydrocarbons by a catalytic isomerization process.

The known technology for improving the octane rating of certain hydrocarbon fractions, especially mixed feedstocks containing normal and iso pentanes and hexanes, typically involves totally isomerizing all normal hydrocarbons in the feed.

According to one widely used process, the entire feed is subjected to an initial catalytic reaction and then a separation procedure employing molecular sieve adsorbers. The adsorbers are then purged to desorb normals, and desorbed normals and purge gas are recycled to the isomerization reactor. This is known as a reactor-lead process.

According to another known process, the feed is first passed to the adsorbers which immediately remove non-normals. The normals are then isomerized, with subsequent removal of newly-formed non-normals and full recycle of normals to the reactor. This is known in the art as an adsorber-lead process.

By virtue of the total recycle of all unisomerized normals in both the adsorber-lead and reactor-lead formats, these processes will eventually totally isomerize all normal pentanes and hexanes in the feed. However, the recycle flow rates create the need for excessively large reactors, adsorbers, furnaces, and purge gas recycle equipment which is extremely costly not only on initial investment, but also on an operational basis.

BACKGROUND ART

In Canadian Pat. No. 1,064,056, Reber et al describe a total isomerization process wherein large fluctuations in the concentration of either n-pentane or n-hexane in the reactor feed are prevented by suitably controlling the operation of a three-bed adsorber system. According to the disclosure, no more than two beds are being desorbed at any given time and the terminal stage of desorption in one of the three beds is contemporaneous with the initial stage of desorption in another of the three beds.

Both adsorber-lead and reactor-lead processes are then specifically exemplified. The adsorber-lead process calls for first passing a combined feed comprised of fresh feed and the total reactor effluent through the adsorbers to remove non-normal hydrocarbons so that the feed to the reactor is essentially normal hydrocarbons. This requires adsorbers of significant size and large recycle inventories which, in turn, require larger reactor volumes.

In U.S. Pat. No. 4,210,771, Holcombe describes a reactor-lead total isomerization process which reduces the recycle rate to the reactor while still maintaining a sufficient hydrogen partial pressure to protect the catalyst against coking. The partial pressure of the hydrogen in the reactor is a function of the hydrogen concentration. The system maintains the flow rates of hydrogen in the recycle and the combined reactor feed at constant levels, and varies the flow rate of fresh feed in an inverse relationship with desorbed normals in the recycle. By thus eliminating fluctuations in hydrocarbon flow rates to the reactor, the recycle flow rate to the reactor is reduced without risking an insufficient partial pressure of hydrogen to protect the catalyst. However, this reactor-lead process required recycle of all normal hydrocarbons, and the reactor, adsorber and recycle system capacities sufficient in size to accommodate this.

It would be desirable to reduce recycle flow rates and operate smaller reactors and adsorbers, and to otherwise improve operating efficiencies based on constant throughputs while still significantly increasing the octane of the feed hydrocarbon.

SUMMARY OF THE INVENTION

It has been determined according to the present invention that by modifying one of the known total isomerization processes, significant economies can be achieved while still producing an increased octane product suitable as a base stock for use in blending gasoline. The modification enables reduction in adsorber, reactor and hydrocarbon recycle sizes in greater proportion than the octane rating of the product. The present invention is based on the discovery that by implementing the changes in the adsorber-lead process, in a manner counter to conventional technology, an unexpectedly large ratio of octane increase to capital investment can be achieved.

The present invention provides a process and an apparatus for upgrading the octane of a hydrocarbon feed containing non-normal hydrocarbon compounds and normal pentane and hexane, comprising: passing said hydrocarbon feed to an adsorption section containing an adsorber bed to adsorb normal hydrocarbons from said feed and to pass non-normal hydrocarbons out of the adsorption section as adsorber effluent; passing a purge gas through said adsorber bed containing adsorbed normal hydrocarbons to produce a desorption effluent comprising purge gas and normal hydrocarbons; passing said desorption effluent through an isomerization reactor to produce a reactor effluent comprising purge gas and reactor hydrocarbon product comprising non-normal and normal hydrocarbons; combining at least a portion of said reactor hydrocarbon product with said adsorber effluent to form an enriched octane product stream comprising normal and non-normal hydrocarbons; and separating and recycling said purge gas to said adsorption section.

Preferably, from 50 to 100% of said reactor hydrocarbon product is combined with said adsorber effluent. In the most economical system to install and operate, the entire reactor hydrocarbon product is combined with said adsorber effluent. With some increased costs, but with advantages in terms of process flexibility, up to 50% of the reactor hydrocarbon product can be combined with the fresh feed and recycled to the adsorber.

The apparatus of the invention comprises: an adsorption section containing an adsorber bed containing a solid adsorbent therein capable of adsorbing normal hydrocarbons from a feed of the type described; means for feeding said hydrocarbon feed to an adsorption section; means for passing non-normal hydrocarbons out of said adsorption section as adsorber effluent; means for passing a purge gas through said adsorber bed containing adsorbed normal hydrocarbons to produce desorption effluent comprising purge gas and normal hydrocarbons; means for passing said desorption effluent to and isomerization reactor; an isomerization reactor containing an isomerization catalyst capable of isomerizing normal hydrocarbons to non-normal hydrocarbons and to produce a reactor effluent comprising a mixture of purge gas and normal and non-normal hydrocarbons; means for combining at least a portion of said reactor product stream with said adsorber effluent to form an enriched octane product stream comprising normal and non-normal hydrocarbons; and means for separating and recycling said purge gas to said adsorption section.

DESCRIPTION OF THE DRAWINGS

The invention will be better understood and its advantages will be more apparent from the following detailed description when read in connection with the accompanying drawings wherein.

DETAILED DESCRIPTION

The invention will be described primarily according to its preferred embodiment wherein a mixed hydrocarbon feedstock (fresh feed) is upgraded for use as a gasoline blending stock by a simplified combination of adsorption and isomerization steps, in an adsorber-lead configuration. By virtue of its simplicity, the present invention enables the reduction in the size of the adsorbers, the isomerization reactor, furnaces required for heating process streams, and purge gas recycle equipment. The significance of these reduced sizes versus the high productivity maintained is unexpected.

Figure 1:
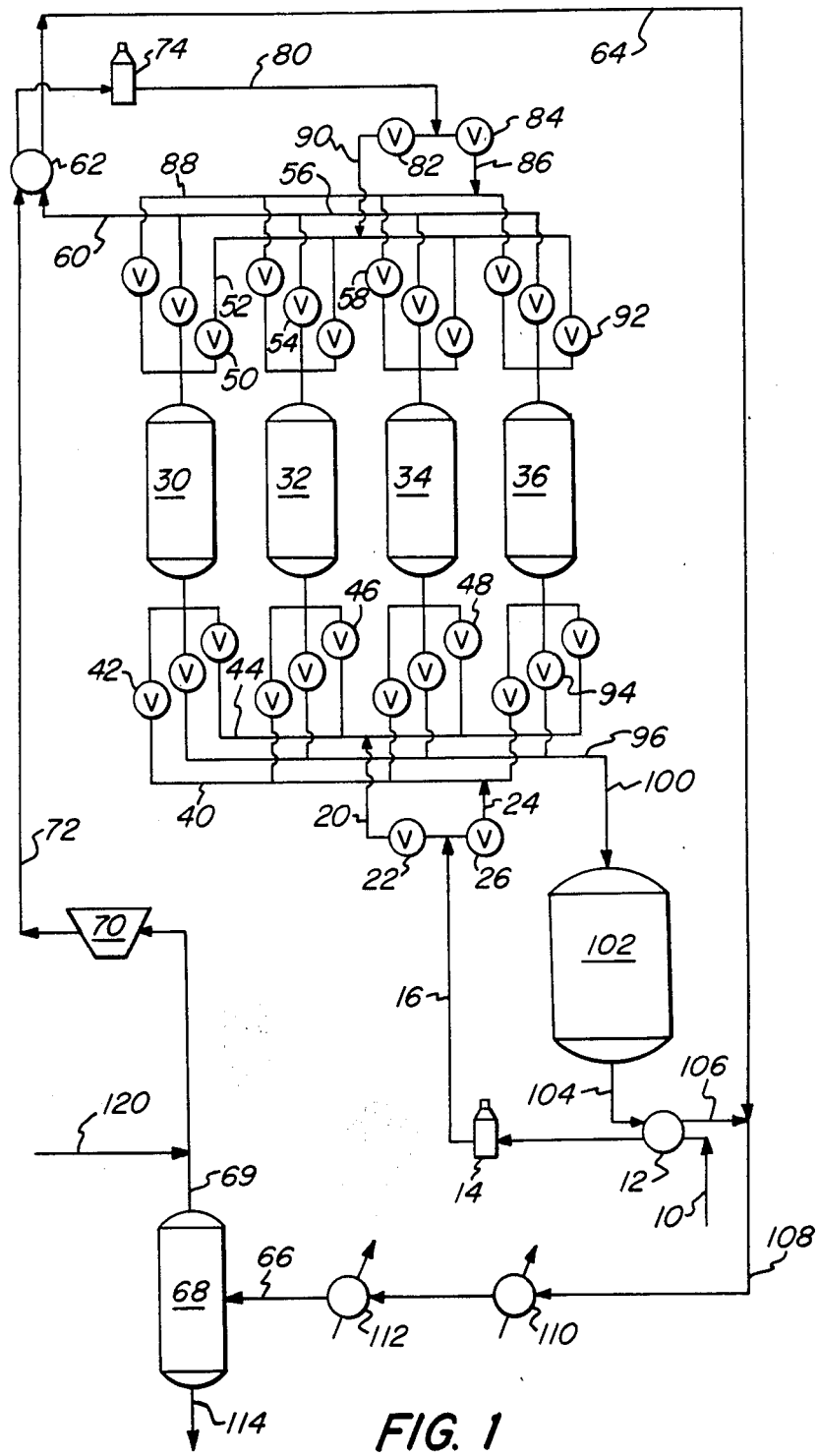
FIG. 1 is a schematic of a process and apparatus arrangement according to the invention wherein the entire isomerization reactor hydrocarbon product is combined with the adsorber affluent as an enhanced octane hydrocarbon.

A mixed hydrocarbon feedstock (fresh feed) is fed via line 10 as required for the process. The feedstock in the embodiment of FIG. 1 is fresh feed to the process and contains normal and non-normal hydrocarbons. It is composed principally of the various isomeric forms of saturated hydrocarbons having from five to six carbon atoms. The expression "the various isomeric forms" is intended to denote all the branched chain and cyclic forms of the noted compounds, as well as the straight chain forms. Also, the prefix notations "iso" and "i" are intended to be generic designations of all branched chain and cyclic (i.e., non-normal) forms of the indicated compound.

The following composition is typical of a feedstock suitable for processing according to the invention:

| Components | Mole % |
| --- | --- |
| $C_4$ and lower | 0–7 |
| i-$C_5$ | 10–40 |
| n-$C_5$ | 5–30 |
| i-$C_6$ | 10–40 |
| n-$C_6$ | 5–30 |
| $C_7$ and higher | 0–10 |

Suitable feedstocks are typically obtained by refinery distillation operations, and may contain small amounts of $C_7$ and even higher hydrocarbons, but these are typically present, if at all, only in trace amounts. Olefinic hydrocarbons are advantageously less than about 4 mole percent in the feedstock. Aromatic and cycloparaffin molecules have a relatively high octane number. Accordingly, the preferred feedstocks are those high in aromatic and cycloparaffinic hydrocarbons, e.g., at least 5, and more typically from 10 to 25 mole percent of these components combined.

The non-cyclic $C_5$ and $C_6$ hydrocarbons typically comprise at least 60, and more typically at least 75, mole percent of the feedstock, with at least 25, and preferably at least 35, mole percent of the feedstock being hydrocarbons selected from the group of iso-pentane, iso-hexane and combinations of these. Preferably, the feedstock will comprise no more than 40, and more preferably no more than 30 mole percent of a combination of n-pentane and n-hexane.

Referring again to FIG. 1, fresh feed in line 10 is heated by indirect heat exchange with reactor effluent in heat exchanger 12 from which it is passed to furnace 14 where it is heated sufficiently for passage to the adsorption section via line 16.

Adsorber feed from line 16 and furnace 14 is directed partially to line 20 by way of pressure control valve 22 and partially to line 24 by means of flow rate control valve 26. From these lines, the adsorber feed stream is directed to the appropriate bed in the adsorption section.

The adsorber feed, containing normal and non-normal hydrocarbons in the vapor state is passed at superatmospheric pressure periodically in sequence through each of a plurality of fixed adsorber beds, e.g., four as described in U.S. Pat. No. 3,700,589 or three as described in U.S. Pat. No. 3,770,621, of an adsorption section containing a zeolitic molecular sieve adsorbent. These U.S. patents are incorporated by reference herein in their entireties.

Preferably, the adsorbents have effective pore diameters of substantially 5 Angstroms. The term "bed void space" for purposes of this description means any space in the bed not occupied by solid material except the intracrystalline cavities of the zeolite crystals. The pores within any binder material which may be used to form agglomerates of the zeolite crystals is considered to be bed void space. In a four bed system, each of the beds cyclically undergoes the stages of:

A-1 adsorption-fill, wherein the vapor in the bed void space consists principally of a non-sorbable purge gas and the incoming feedstock forces the said non-sorbable purge gas from the bed void space out of the bed without substantial intermixing thereof with non-adsorbed feedstock fraction;

A-2 adsorption, wherein the feedstock is cocurrently passed through said bed and the normal constituents of the feedstock are selectively adsorbed into the internal cavities of the crystalline zeolitic adsorbent and the non-adsorbed constituents of the feedstock are removed from the bed as an effluent having a greatly reduced content of non-feedstock constituents;

D-1 void space purging, wherein the bed loaded with normals adsorbate to the extent that the stoichiometric point of the mass transfer zone thereof has passed between 85 and 97 percent of the length of the bed and containing in the bed voids space a mixture of normals and non-normals in essentially feedstock proportions, is purged countercurrently, with respect to the direction of A-2 adsorption by passing through the bed a stream of a non-sorbable purge gas in sufficient quantity to remove said void space feedstock vapors but not more than that which produces about 50 mole percent, preferably not more than 40 mole percent, of adsorbed feedstock normals in the bed effluent; and D-2 purge desorption, wherein the selectively adsorbed feedstock normals are desorbed as part of the desorption effluent by passing a non-sorbable purge as countercurrently with respect to A-2 adsorption through the bed until the major proportion of adsorbed normals has been desorbed and the bed void space vapors consist principally of non-sorbable purge gas, e.g., a hydrogen-containing recycle stream which comprises hydrogen and light hydrocarbons.

The zeolitic molecular sieve employed in the adsorption bed must be capable of selectively adsorbing the normal paraffins of the feedstock using molecular size and configuration as the criterion. Such a molecular sieve should, therefore, have an apparent pore diameter of less than about 6 Angstroms and greater than about 4 Angstroms. A particularly suitable zeolite of this type is zeolite A, described in U.S. Pat. No. 2,883,243, which in several of its divalent exchanged forms, notably the calcium cation form, has an apparent pore diameter of about 5 Angstroms, and has a very large capacity for adsorbing normal paraffins. Other suitable molecular sieves include zeolite R, U.S. Pat. No. 3,030,181; zeolite T, U.S. Pat. No. 2,950,952, and the naturally occurring zeolitic molecular sieves chabazite and erionite. These U.S. patents are incorporated by reference herein in their entireties.

The term "apparent pore diameter" as used herein may be defined as the maximum critical dimension, or the molecular species which is adsorbed by the adsorbent under normal conditions. The critical dimension is defined as the diameter of the smallest cylinder which will accommodate a model of the molecule constructed using the available values of bond distances, bond angles and van der Waals' radii. The apparent pore diameter will always be larger than the structural pore diameter, which can be defined as the free diameter of the appropriate silicate ring in the structure of the adsorbent.

Referring again to the drawing, and the adsorption section in particular, the following description details an operation wherein bed 30 is undergoing A-1 adsorption-fill; bed 32, A-2 adsorption; bed 34, D-1 void space purging; and bed 36, D-2 purge desorption. A portion of the adsorber feed from line 16 is directed via line 24 through manifold 40 and valve 42 to adsorption bed 30 undergoing A-1 adsorption. Each of the four adsorption beds in the system, namely beds 30, 32, 34 and 36 contain a molecular sieve adsorbent in a suitable form such as cylindrical pellets.

Bed 30, at the time that feed passing through valve 42 enters, contains residual purge gas from the preceding desorption stroke. As will be explained in detail later, the purge gas is typically hydrogen-containing because of the need to maintain at least a minimum hydrogen partial pressure in the isomerization reactor. This is supplied to the adsorbers during desorption as a purge gas recycle stream via line 80. The rate of flow of the adsorber feed through line 24, manifold 40 and valve 42 is controlled such that bed 44 is flushed of residual hydrogen-containing purge gas adsorber stage time period of from about thirty seconds to about two minutes.

During this first stage of adsorption in bed 30, the hydrogen-containing purge gas effluent passes from the bed through valve 50 into manifold 52. During the time period when the hydrogen-containing purge gas is being flushed from bed 30, the remaining adsorber feed passes through valve 22 and line 20, through manifold 44, and valve 46 to bed 32.

The normal paraffins in the feed are adsorbed by bed 32 undergoing A-2 adsorption and an adsorber effluent, i.e., the non-adsorbed non-normals, emerges from the bed through valve 54 and from there is fed to manifold 56. The adsorber effluent flows through line 60, heat exchanger 62, and line 64, for combination with at least a portion of the reactor hydrocarbon product as final product. The embodiment of FIG. 1 will employ all reactor hydrocarbon product in the final product, while the embodiment of FIG. 2 will employ a portion, e.g., at least 50%.

Figure 2:
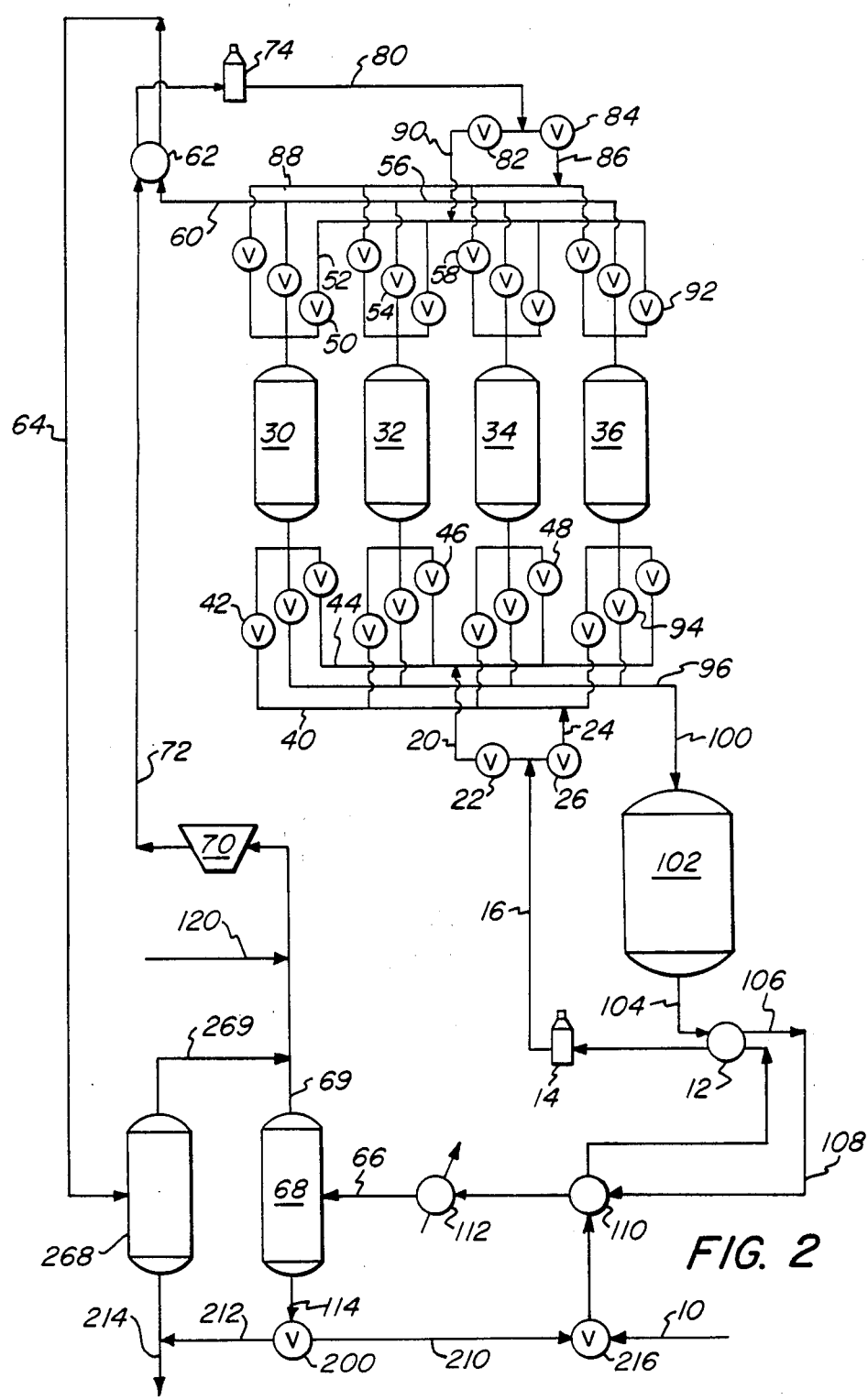
FIG. 2 is a schematic of another process and apparatus arrangement which enables withdrawal of a portion of the isomerization reactor hydrocarbon product for combining with the adsorber effluent while returning a limited amount of the reactor product to the adsorbers.

In FIG. 1, the purge gas can be recovered from the combined product stream 66 by separator 68 and then fed via line 69 to recycle compressor 70 for return to the adsorption section. In the embodiment of FIG. 2, the purge gas is shown to be separated from the reactor hydrocarbon product prior to combining the latter with the non-normal hydrocarbons from the adsorber effluent.

During the adsorber stage time period when the residual hydrogen-containing purge gas is being flushed from bed 30, i.e., A-1 adsorption, bed 34 is undergoing the first stage of purging wherein the hydrocarbons in the bed void space are being flushed from the bed, i.e., D-1 purging. During the same time period, bed 36 is undergoing the second stage of desorption, i.e., D-2 purge desorption, in which the normal hydrocarbons are desorbed from the molecular sieve adsorbent using hydrogen-containing recycle purge gas stream and removed from the bed.

From compressor 70, the hydrogen-containing purge gas stream from separator 68 is passed through line 72 and heat exchanger 62 and heater 74, wherein it is heated and then passed through line 80 as the purge gas recycle stream. The pressure of the adsorbers will typically be within the range of from 200 to 320 psia, and preferably will be in the range of from 240 to 300 psia.

The hydrogen-containing purge gas recycle stream from line 80 can be divided into two streams by means of flow control valves 82 and 84, and the lesser stream passed through line 86, manifold 88, and valve 58 countercurrently (with respect to the previous adsorption stroke) through bed 34. The low, controlled flow rate employed for the first stage desorption is for the purpose of flushing non-adsorbed hydrocarbons from the bed voids without causing excessive desorption of the normals from the adsorbent.

The effluent from bed 34, passes through valve 48 and into manifold 44 where it is recycled through valve 46 directly to bed 32 undergoing A-2 adsorption. The major portion of the hydrogen recycle stream from line 80 is passed through control valve 82, line 90, to manifold 52 where it is mixed with the previously mentioned first stage adsorption effluent from valve 50 and then passes through valve 92 and bed 36. During this stage, selectively-adsorbed normal paraffins are desorbed from the zeolitic molecular sieve and flushed from the bed. The adsorption effluent from bed 36, comprising hydrogen and desorbed normal paraffins, passes through valve 94 and manifold 96 to line 100, from which it is sent to isomerization reactor 102 as reactor feed.

The foregoing description is for a single adsorber stage time period of a total four stage cycle for the system. For the next adsorber stage time period, appropriate valves are operated so that bed 30 begins A-2 adsorption, bed 32 begins D-1 purging, bed 34 begins D-2 desorption, and bed 36 begins A-1 adsorption. Similarly, a new cycle begins after each adsorber stage time period; and, at the end of the four cycle time periods, all the beds have gone through all stages of adsorption and desorption.

The following chart indicates the functioning of each of the four beds for adsorption stage cycle times of one minute:

| Time, min. | 0–1 | 1–2 | 2–3 | 3–4 |
|---|---|---|---|---|
| Bed 30 | A-1 | A-2 | D-1 | D-2 |
| Bed 32 | A-2 | D-1 | D-2 | A-1 |
| Bed 34 | D-1 | D-2 | A-1 | A-2 |
| Bed 36 | D-2 | A-1 | A-2 | D-1 |

The isomerization process will result in some hydrogen losses from the purge gas due to hydrogenation of starting materials and cracked residues. Hydrogen will also be lost due to solubility in product, and possibly a vent from line 69 (not shown) which can be controlled by suitable valve means. These losses require the addition of makeup hydrogen. Makeup hydrogen can be supplied in impure form, typically as an offgas from catalytic reforming or steam reforming of methane. These hydrogen sources are suitably pure for isomerization processes which typically have a vent from the recycle stream. Refinery streams of lesser purity may also be satisfactory. The desorption effluent in line 100 will comprise desorbed normal hydrocarbons, e.g., n-pentane and n-hexane, and hydrogen and light hydrocarbon and other impurities which comprise the purge gas used for desorption. This effluent is reactor feed and is passed to isomerization reactor 102.

The isomerization reactor 102 contains an isomerization catalyst which can be any of the various molecular sieve based catalyst compositions well known in the art which exhibit selective and substantial isomerization activity under the operating conditions of the process. As a general class, such catalysts comprise the crystalline zeolitic molecular sieves having an apparent pore diameter large enough to adsorb neopentane, $SiO_2/Al_2O_3$ molar ratio of greater than 3; less than 60, preferably less than 15, equivalent percent alkali metal cations and having those $AlO_4$-tetrahedra not associated with alkali metal cations either not associated with any metal cation, or associated with divalent or other polyvalent metal cations.

Because the feedstock may contain some olefins and will undergo at least some cracking, the zeolitic catalyst is preferably combined with a hydrogenation catalyst component, preferably a noble metal of group VIII of the Periodic Classification of the Elements. The catalyst composition can be used alone or can be combined with a porous inorganic oxide diluent as a binder material. The hydrogenation agent can be carried either on the zeolitic component and/or on the binder. A wide variety of inorganic oxide diluent materials are known in the art—some of which exhibit hydrogenation activity per se. It will, accordingly, be understood that the expression "an inorganic diluent having a hydrogenation agent thereon" is meant to include both diluents which have no hydrogenation activity per se and carry a separate hydrogenation agent and those diluents which are per se hydrogenation catalysts. Oxides suitable as diluents, which of themselves exhibit hydrogenation activity, are the oxides of the metals of Group VI of the Mendeleev Periodic Table of Elements. Representative of the metals are chromium, molybdenum and tungsten.

It is preferred that the diluent material possess no pronounced catalytic cracking activity. The diluent should not exhibit a greater quantitative degree of cracking activity than the zeolitic component of the overall isomerization catalyst composition. Suitable oxides of this latter class are the aluminas, silicas, the oxides of metals of Groups III, IV-A and IV-B of the Mendeleev Periodic Table, and cogels of silica and oxides of the metals of the Groups III, IV-A and IV-B, especially alumina, zirconia, titania, thoria and combinations thereof. Aluminosilicate clays such as kaolin, attapulgite, sepiolite, polygarskite, bentonite, montmorillonite, and the like, when rendered in a pliant plastic-like condition by intimate admixture with water are also suitable diluent materials, particularly when said clays have not been acid-washed to remove substantial quantities of alumina.

Suitable catalysts for isomerization reactions are disclosed in detail in U.S. Pat. Nos. 3,236,761 and 3,236,762. A particularly preferred catalyst is one prepared from a zeolite Y (U.S. Pat. No. 3,130,007) having a $SiO_2/Al_2O_3$ molar ratio of about 5 by reducing the sodium cation content to less than about 15 equivalent percent by ammonium cation exchange, then introducing between about 35 and 50 equivalent percent of rare earth metal cations by ion exchange and thereafter calcining the zeolite to effect substantial deammination. As a hydrogenation component, platinum or palladium in an amount of about 0.1 to 1.0 weight percent, can be placed on the zeolite by any conventional method. The disclosures of these above-cited U.S. patents are incorporated herein by reference in their entireties.

Depending on the particular catalyst composition employed, the operating temperature of the isomerization reactor is generally within the range of 200° to 390° C. and the pressure is within the range of 175 to 600 psia., desirably from 200 to 300, preferably 220 to 260 psia, and most preferably less than 250 psia. The reactor is maintained under a hydrogen partial pressure sufficient to prevent coking of the isomerization catalyst at the conditions maintained in the reactor. Typically, the hydrogen partial pressure will be within the range of from 100 to 250, preferably from 130 to 190, psia with the hydrogen, on the average, comprising from 45 to 80, preferably from 60 to 80 and most preferably from 65 to 80, mole percent of the reactor contents which are maintained in a gaseous state.

The feed to the reactor will contain, in addition to hydrogen and hydrocarbon reactants, e.g., normal and iso pentane and hexane, a quantity of light hydrocarbons which are produced during the reaction and possibly as part of feed and makeup. Because these are nonsorbable, they are retained in the process at some equilibrium level and circulate with the recycle stream.

Referring again to the FIG. 1, the effluent from the reactor 102 flows via line 104 through heat exchanger 12 where its sensible heat is used to heat fresh feed. From the heat exchanger 12, the reactor effluent is transferred via line 106 for combination with adsorption effluent in line 64. The combined stream of reactor effluent and adsorption effluent, line 108, is then cooled by means of one or more coolers 110 and 112 prior to passage via line 66 to separator 68. Separator 68 forms a liquid fraction which is withdrawn via line 114 as product which is enriched in octane and suitable for employing as a gasoline blending stock, and a gas fraction which is withdrawn via line 69 for recycle to the adsorbers. Make-up purge gas, preferably hydrogen or a hydrogen-containing gas, is added as needed via line 120. The product is increased in research octane number (RON) by at least two units, and preferably at least six units. The ratio of fresh feed weight to catalyst weight is at least 2.75 hour$^{-1}$, preferably at least 3.0 hour$^{-1}$, and most preferably from 3.0 to 5.0 hour$^{-1}$.

The embodiment of FIG. 2 modifies that of FIG. 1 by providing means capable of directing a portion of the reactor hydrocarbon product from line 114 to be combined with fresh feed. As shown in FIG. 2, the reactor hydrocarbon product is fed via line 114 to valve 200 which is suitably controlled to direct a portion, preferably variable from 0 to 50%, of that product into line 210 and remainder via line 212 to the final product stream 214. The hydrocarbon stream line 210 is combined with fresh feed by suitably-controlled means which may include valve 216.

Further in explanation of the modifications of the embodiment shown in FIG. 1 which are necessary to facilitate this aspect of the invention, the adsorber effluent is passed via line 64 to separator 268 which provides a liquid fraction containing primarily non-normal hydrocarbons taken off at line 214 and a gaseous fraction containing primarily purge gas for recycle which is taken off at line 269. It is an advantage of this embodiment that variations in the product octane can be obtained from feeds of constant octane and that a relatively constant octane product can be achieved from feeds of varying octane while still retaining the most significant advantages of the invention.

It is an advantage of both embodiments that existing total isomerization equipment can be modified according to the invention to greatly increase feed throughput and final product production while still providing octane values sufficient for use as a gasoline blending stock.

The following examples will help to illustrate and explain the invention, but are not meant to be limiting in any regard. Unless otherwise indicated, all parts and percentages are on a molar basis.

EXAMPLE 1

This example illustrates the operation of a process essentially as shown in FIG. 1 to increase the octane of a hydrocarbon feed having the following composition and having a research octane number of 77:

| Components | Parts (Molar) |
| --- | --- |
| i-butane | 0.7 |
| n-butane | 4.6 |
| i-pentane | 16.3 |
| n-pentane | 15.7 |
| cyclopentane | 2.4 |
| 2,2-dimethyl butane | 0.8 |
| 2,3-dimethyl butane | 2.1 |
| 2-methyl pentane | 10.0 |
| 3-methyl pentane | 12.3 |
| n-hexane | 11.9 |
| methyl cyclopentane | 7.4 |
| cyclohexane | 4.4 |
| benzene | 9.2 |
| n-heptane | 2.0 |

The hydrocarbon is fed to an adsorber section as described above at a pressure of 240 psia and a rate of 52,844 pounds per hour. Each bed in the adsorber contains 30,904 pounds of a calcium zeolite A adsorbent in the form of 1/16 inch cylindrical pellets. Adsorption effluent is produced at an average flow rate of 35,270 pounds per hour and has the following average composition:

| Components | Parts (Molar) |
| --- | --- |
| hydrogen | 19.1 |
| methane | 1.7 |
| ethane | 0.2 |
| propane | 0.2 |
| i-butane | 1.0 |
| n-butane | 2.9 |
| i-pentane | 18.4 |
| n-pentane | 1.0 |
| cyclopentane | 2.7 |
| 2,2-dimethyl butane | 1.0 |
| 2,3-dimethyl butane | 2.4 |
| 2-methyl pentane | 11.4 |
| 3-methyl pentane | 13.9 |
| n-hexane | 0.2 |
| methyl cyclopentane | 8.4 |
| cyclohexane | 5.0 |
| benzene | 10.4 |
| n-heptane | 0.1 |

The adsorber bed, after adsorption of normal hydrocarbons from the feed, is desorbed with a purge gas stream having average recycle flow rate of 11,737 pounds per hour, which contains principally hydrogen (85.3%) and methane (7.6%).

The desorption effluent has an average flow rate of 29,311 pounds, pressure from the bed being desorbed of 236 psia, and composition as follows:

| Components | Parts (Molar) |
| --- | --- |
| hydrogen | 73.6 |
| methane | 6.5 |
| ethane | 0.7 |
| propane | 0.9 |
| i-butane | 0.7 |
| n-butane | 1.6 |
| i-pentane | 2.0 |
| n-pentane | 6.2 |
| cyclopentane | 0.1 |
| 2,2-dimethyl butane | 0.1 |
| 2,3-dimethyl butane | 0.1 |
| 2-methylpentane | 0.5 |
| 3-methyl pentane | 0.6 |
| n-hexane | 4.6 |
| methyl cyclopentane | 0.3 |
| cyclohexane | 0.2 |
| benzene | 0.4 |
| C$_7$ | 0.8 |

The desorption effluent is fed to a reactor containing 13,075 pounds of a zeolite Y catalyst support in which the zeolite has a molar S:O$_2$/Al$_2$O$_3$ ratio of 5, a sodium cation for operation of about 10 equivalent percent, and containing 667 troy ounces of platinum. The reactor is operated at a pressure of about 230 psia and a temperature of about 500° F., with the desorption effluent being fed at an average rate of about 29,311 pounds per hour.

Upon passing through the reactor, the reactor effluent has the following composition:

| Components | Parts (Molar) |
| --- | --- |
| hydrogen | 72.4 |
| methane | 6.7 |
| ethane | 0.8 |
| propane | 1.5 |
| i-butane | 1.7 |

-continued

| Components | Parts (Molar) |
|---|---|
| n-butane | 1.8 |
| i-pentane | 5.2 |
| n-pentane | 3.1 |
| cyclopentane | 0.1 |
| 2,2-dimethyl butane | 1.1 |
| 2,3-dimethyl butane | 0.5 |
| 2-methyl pentane | 1.9 |
| 3-methyl pentane | 1.3 |
| n-hexane | 1.2 |
| methyl cyclopentane | 0.3 |
| cyclohexane | 0.1 |
| $C_7$ | 0.4 |

The reactor effluent and the adsorption effluent are combined and the combined stream is then separated into a purge gas recycle stream and a final product stream. The final product is produced at an average rate of 53,193 pounds per hour and has the following composition:

| Components | Parts (Molar) |
|---|---|
| hydrogen | 1.1 |
| methane | 0.7 |
| ethane | 0.4 |
| propane | 1.6 |
| i-butane | 3.2 |
| n-butane | 4.8 |
| i-pentane | 23.3 |
| n-pentane | 7.4 |
| cyclopentane | 2.3 |
| 2,2-dimethyl butane | 3.0 |
| 2,3-dimethyl butane | 3.0 |
| 2-methyl pentane | 13.0 |
| 3-methyl pentane | 13.4 |
| n-hexane | 2.9 |
| methyl cyclopentane | 7.1 |
| cyclohexane | 4.1 |
| benzene | 7.9 |
| $C_7$ | 0.5 |

The product has a research octane number of 85, an increase of 8, very suitable as a gasoline blending stock. And, this product is produced with the high ratio of feed weight to catalyst weight of greater than 4.0 hour$^{-1}$.

EXAMPLE 2

This example details the processing of a fresh feed as shown in Example 1 according to process sequence shown in FIG. 2. Accordingly, the feed to the adsorption section further includes 50% by weight of the reactor hydrocarbon product. To accommodate the larger combined feed, the adsorber section contains a total of 174,695 pounds of the same zeolite adsorbent, and the reactor contains 17,451 pounds of zeolite catalyst base and 890 troy ounces of platinum. The final product is produced at 53,203 pounds per hour and has the following composition:

| Components | Parts (Molar) |
|---|---|
| hydrogen | 1.1 |
| methane | 0.7 |
| ethane | 0.4 |
| propane | 1.8 |
| i-butane | 3.6 |
| n-butane | 4.8 |
| i-pentane | 25.5 |
| n-pentane | 5.0 |
| cyclopentane | 2.3 |
| 2,2-dimethyl butane | 3.1 |

-continued

| Components | Parts (Molar) |
|---|---|
| 2,3-dimethyl butane | 3.1 |
| 2-methyl pentane | 13.3 |
| 3-methyl pentane | 13.7 |
| n-hexane | 1.7 |
| methyl cyclopentane | 7.0 |
| cyclohexane | 4.0 |
| benzene | 8.0 |
| $C_7$ | 0.5 |

The final product in this case has a research octane number of 87, an increase of 10, again highly suited as a gasoline blending stock. And, this product is produced with the high ratio of feed weight to catalyst weight of about 3.0 hour$^{-1}$.

The above description is for the purpose of teaching the person of ordinary skill in the art how to practice the present invention and is not intended to detail all of those obvious modifications and variations of it which will become apparent to the skilled worker upon reading the description. It is intended, however, that all such modifications and variations be included within the scope of the present invention which is defined by the following claims.

We claim:

1. A process for upgrading the octane of a hydrocarbon feed containing non-normal hydrocarbon compounds and normal pentane and hexane, comprising:
   (a) passing said hydrocarbon feed to an adsorption section containing an adsorber bed to adsorb normal hydrocarbons from said feed, and to pass non-normal hydrocarbons out of the adsorption section as adsorber effluent;
   (b) passing purge gas through said adsorber bed containing adsorbed normal hydrocarbons to produce a desorption effluent comprising purge gas and normal hydrocarbons;
   (c) passing said desorption effluent through an isomerization reactor to produce a reactor effluent comprising purge gas and reactor hydrocarbon product comprising non-normal and normal hydrocarbons;
   (d) combining at least a portion of said reactor product stream with said adsorber effluent to form an enriched octane product stream comprising normal and non-normal hydrocarbons; and
   (e) separating and recycling said purge gas to said adsorption section.

2. A process according to claim 1 wherein from 50 to 100% of said reactor hydrocarbon product is combined with said adsorber effluent.

3. A process according to claim 2 wherein all of said reactor hydrocarbon product is combined with said adsorber effluent.

4. A process according to claim 2 wherein up to 50% of said reactor hydrocarbon product is combined with said feed and passed to said adsorption section.

5. A process according to claim 1 wherein said hydrocarbon feed comprises from 5 to 25 mole percent aromatic and cycloparaffinic hydrocarbons and at least 35 mole percent of hydrocarbons selected from the group of iso-pentane, iso-hexane and combinations of these.

6. A process according to claim 5 wherein said hydrocarbon feed comprises no more than 40 mole percent of a combination of n-pentane and n-hexane.

7. A process according to claim 6 wherein said feed comprises at least 60 mole percent non-cyclic $C_5$ and $C_6$ hydrocarbons and no more than 30 mole percent of a combination of n-pentane and n-hexane.

8. A process according to claim 6 wherein the weight ratio of said feed to catalyst in said reactor is greater than 2.75 hour$^{-1}$.

9. A process for upgrading by at least two research octane number units a hydrocarbon feed having the following composition

| Components | Mole % |
|---|---|
| C$_4$ and lower | 0–7 |
| i-C$_5$ | 10–40 |
| n-C$_5$ | 5–30 |
| i-C$_6$ | 10–40 |
| n-C$_6$ | 5–30 |
| C$_7$ and higher | 0–10 | the process comprising:
(a) passing said hydrocarbon feed to an adsorption section containing an adsorber bed to adsorb normal hydrocarbons from said feed, and to pass non-normal hydrocarbons out of the adsorption section as adsorber effluent;
(b) passing purge gas through said adsorber bed containing adsorbed normal hydrocarbons to produce a desorption effluent comprising purge gas and normal hydrocarbons;
(c) passing said desorption effluent through an isomerization reactor to produce a reactor effluent comprising purge gas and reactor hydrocarbon product comprising non-normal and normal hydrocarbons, said reactor containing an isomerization catalyst in an amount sufficient to provide a weight ratio of said feed to said catalyst of greater than 2.75 hour$_{-1}$;
(d) combining at least a portion of said reactor product stream with said adsorber effluent to form an enriched octane product stream comprising normal and non-normal hydrocarbons; and
(e) separating and recycling said purge gas to said adsorption section.

10. A process according to claim 9 wherein from 50 to 100% of said reactor hydrocarbon product is combined with said adsorber effluent.

11. A process according to claim 10 wherein all of said reactor hydrocarbon product is combined with said adsorber effluent.

12. A process according to claim 10 wherein up to 50% of said reactor hydrocarbon product is combined with said feed and passed to said adsorption section.

13. A process according to claim 9 wherein said hydrocarbon feed comprises from 5 to 25 mole percent aromatic and cycloparaffinic hydrocarbons and at least 35 mole percent of hydrocarbons selected from the group of iso-pentane, iso-hexane and combinations of these.

14. A process according to claim 13 wherein said hydrocarbon feed comprises no more than 40 mole percent of a combination of n-pentane and n-hexane.

15. A process according to claim 14 wherein said feed comprises at least 60 mole percent non-cyclic C$_5$ and C$_6$ hydrocarbons and no more than 30 mole percent of a combination of n-pentane and n-hexane.

16. A process according to claim 15 wherein the research octane number of said enriched octane product stream is at least six units greater than that of said feed.

17. A process according to claim 8 wherein the weight ratio of feed to catalyst in said reactor is greater than about 3.0 hour$^{-1}$.

18. A process according to claim 16 wherein the weight ratio of feed to catalyst in said reactor is at least 4.0 hour$^{-1}$.

19. An apparatus for upgrading the octane of a hydrocarbon feed containing non-normal hydrocarbon compounds and normal pentane and hexane, comprising:
(a) an adsorption section containing an adsorber bed containing a solid adsorbent therein capable of adsorbing normal hydrocarbons from said feed;
(b) means for feeding said hydrocarbon feed to an adsorption section;
(c) means for passing non-normal hydrocarbons out of said adsorption section as adsorber effluent;
(d) means for passing a purge gas through said adsorber bed containing adsorbed normal hydrocarbons to produce desorption effluent comprising purge gas and normal hydrocarbons;
(e) means for passing said desorption effluent to an isomerization reactor;
(f) an isomerization reactor containing an isomerization catalyst capable of isomerizing normal hydrocarbons to non-normal hydrocarbons and to produce a reactor effluent comprising a mixture of purge gas and normal and non-normal hydrocarbons;
(g) means for combining at least a portion of said reactor product stream with said adsorber effluent to form an enriched octane product stream comprising normal and non-normal hydrocarbons; and
(h) means for separating and recycling said purge gas to said adsorption section.

20. An apparatus according to claim 19 which further includes: means for separating up to 50% of said reactor hydrocarbon product prior to combination with said adsorber effluent, and means for passing the separated portion of the reactor hydrocarbon product to said adsorption section.

* * * * *